United States Patent
Hilmersson

(10) Patent No.: US 11,839,492 B2
(45) Date of Patent: Dec. 12, 2023

(54) PRESSURE CATHETER AND GUIDE WIRE ASSEMBLY

(71) Applicant: CAVIS TECHNOLOGIES AB, Uppsala (SE)

(72) Inventor: Mats Hilmersson, Bromma (SE)

(73) Assignee: CAVIS TECHNOLOGIES AB, Uppsala (SE)

(*) Notice: Subject to any disclaimer, the term of this patent is extended or adjusted under 35 U.S.C. 154(b) by 615 days.

(21) Appl. No.: 16/637,255

(22) PCT Filed: Aug. 14, 2018

(86) PCT No.: PCT/SE2018/050820
§ 371 (c)(1),
(2) Date: Feb. 6, 2020

(87) PCT Pub. No.: WO2019/035755
PCT Pub. Date: Feb. 21, 2019

(65) Prior Publication Data
US 2020/0245944 A1    Aug. 6, 2020

(30) Foreign Application Priority Data
Aug. 15, 2017 (SE) .................... 1750993-6

(51) Int. Cl.
*A61M 25/09* (2006.01)
*A61B 5/00* (2006.01)
(Continued)

(52) U.S. Cl.
CPC .......... *A61B 5/6851* (2013.01); *A61B 5/0215* (2013.01); *B21F 15/08* (2013.01);
(Continued)

(58) Field of Classification Search
CPC ...... B23K 2101/04–14; B23K 2101/32; B21F 15/02–08; B21F 45/008;
(Continued)

(56) References Cited

U.S. PATENT DOCUMENTS 4,964,409 A    10/1990   Tremulis
4,967,753 A *  11/1990   Haase ................. A61B 8/12
                                                    600/463

(Continued)

FOREIGN PATENT DOCUMENTS

WO    9962584       12/1999
WO    2017144128    8/2017

OTHER PUBLICATIONS

EP18845994.5, "Extended European Search Report", dated Apr. 15, 2021, 7 pages.
(Continued)

*Primary Examiner* — David J. McCrosky
(74) *Attorney, Agent, or Firm* — Kilpatrick Townsend & Stockton LLP

(57) ABSTRACT

A catheter and guide wire assembly (10) for measurement of blood pressure in a living body, comprising: a proximal tube (11) having a distal end and a proximal end; a distal tube (12) having a distal end and a proximal end, which is connected to the distal end of the proximal tube (11); a fluid-permeable coil (13) having a distal end and a proximal end, which is connected to the distal end of the distal tube (12); a distal tip (14), in which the distal end of the fluid-permeable coil (13) is secured; and a core wire (16), which is attached in the proximal tube (11) and which extends through a portion of the proximal tube (11), the distal tube (12) and the fluid-permeable coil (13), and is secured in the distal tip (14), wherein the distal end of the proximal tube (11) and the proximal end of the distal tube (12) are connected by a butt joint and wherein the core wire (16) is glued or brazed to the
(Continued)

inner wall of the proximal tube (11) at or close to the butt joint.

5 Claims, 1 Drawing Sheet

(51) Int. Cl.
    *A61B 5/0215*     (2006.01)
    *B21F 15/08*     (2006.01)
    *B21F 45/00*     (2006.01)
    *A61M 25/00*     (2006.01)

(52) U.S. Cl.
    CPC ........ *B21F 45/008* (2013.01); *A61M 25/0009* (2013.01); *A61M 2025/0003* (2013.01); *A61M 2025/09083* (2013.01); *A61M 2025/09108* (2013.01); *A61M 2025/09175* (2013.01)

(58) Field of Classification Search
CPC ........ A61B 2090/3925; A61B 18/1492; A61B 2017/1107; A61B 2017/1132; A61B 90/39; A61B 17/11; A61B 18/12; A61B 18/14; A61B 2017/00526; A61B 2018/00577; A61B 5/0215; A61B 5/6851; A61B 5/6852; A61B 1/00089; A61B 1/00096; A61B 1/00119; A61B 1/00121; A61B 1/05; A61B 1/2676; A61B 17/1155; A61B 17/12099; A61B 17/12136; A61B 17/320016; A61B 18/00; A61B 18/22; A61B 2017/00477; A61B 2018/00023; A61B 2018/00184; A61B 2018/00434; A61B 2018/00541; A61B 2018/1253; A61B 2018/126; A61B 2018/1407; A61B 2018/144; A61B 2018/1465; A61B 2050/3008; A61B 2050/3011; A61B 2090/309; A61B 5/0066; A61B 8/0841; A61B 8/12; A61B 1/00; A61B 1/00066; A61B 1/0008; A61B 1/00087; A61B 1/00098; A61B 1/00128; A61B 1/00133; A61B 1/00154; A61B 1/0016; A61B 1/018; A61B 1/041; A61B 1/273; A61B 1/32; A61B 10/0045; A61B 17/00234; A61B 17/0057; A61B 17/02; A61B 17/0218; A61B 17/08; A61B 17/083; A61B 17/10; A61B 17/1114; A61B 17/115; A61B 17/12022; A61B 17/14; A61B 17/142; A61B 17/29; A61B 17/32; A61B 17/32002; A61B 17/32053; A61B 17/32056; A61B 17/3209; A61B 17/3403; A61B 17/3468; A61B 17/42; A61B 17/425; A61B 17/56; A61B 17/7002; A61B 17/7014; A61B 17/7035; A61B 17/7044; A61B 17/7046; A61B 17/7049; A61B 17/7058; A61B 17/7091; A61B 17/88; A61B 17/885; A61B 17/92; A61B 18/02; A61B 18/1477; A61B 18/1482; A61B 18/1485; A61B 2017/00004; A61B 2017/00026; A61B 2017/00084; A61B 2017/00123; A61B 2017/00132; A61B 2017/00137; A61B 2017/00243; A61B 2017/00247; A61B 2017/00336; A61B 2017/00557; A61B 2017/00566; A61B 2017/00575; A61B 2017/00597; A61B 2017/00623; A61B 2017/00818; A61B 2017/00836; A61B 2017/00849; A61B 2017/00876; A61B 2017/07257; A61B 2017/111; A61B 2017/22038; A61B 2017/22051; A61B 2017/22067; A61B 2017/2926; A61B 2017/2929; A61B 2017/320032; A61B 2017/320044; A61B 2017/3413; A61B 2017/3486; A61B 2017/3488; A61B 2018/00005; A61B 2018/00214; A61B 2018/0022; A61B 2018/00273; A61B 2018/00404; A61B 2018/00488; A61B 2018/00559; A61B 2018/00589; A61B 2018/00791; A61B 2018/00898; A61B 2018/00982; A61B 2018/0212; A61B 2018/124; A61B 2018/1246; A61B 2018/141; A61B 2018/1861; A61B 2034/2051; A61B 2034/2063; A61B 2050/0014; A61B 2050/0051; A61B 2050/311; A61B 2090/0813; A61B 2090/3614; A61B 2090/3735; A61B 2090/378; A61B 2090/3782; A61B 2090/3788; A61B 2090/3929; A61B 2217/005; A61B 2217/007; A61B 2218/002; A61B 2218/007; A61B 2503/40; A61B 5/0073; A61B 5/0075; A61B 5/0205; A61B 5/1112; A61B 5/6824; A61B 5/6828; A61B 5/6831; A61B 50/13; A61B 50/30; A61B 50/31; A61B 8/0883; A61B 8/0891; A61B 8/4254; A61B 8/445; A61B 8/481; A61B 90/00; A61B 90/08; A61B 90/30; A61B 90/361; A61B 90/37; A61M 25/005; A61M 25/0012; A61M 25/0108; A61M 2025/0081; A61M 25/0009; A61M 25/0053; A61M 25/0054; A61M 2025/0161; A61M 2025/0163; A61M 2025/0681; A61M 25/00; A61M 25/001; A61M 25/0069; A61M 25/0105; A61M 25/0133; A61M 25/0662; A61M 25/09; A61M 25/10; A61M 39/10; A61M 5/178; A61M 5/31; A61M 2025/0003; A61M 2025/09083; A61M 2025/091; A61M 2025/09108; A61M 2025/09175; A61M 2025/1093; A61M 2039/1044; A61M 2039/1061; A61M 2039/267; A61M 25/0014; A61M 25/0097; A61M 39/00; A61M 39/1011; A61M 39/12; A61M 39/165; A61M 39/18; A61M 39/20; A61M 39/26; A61M 2025/0059; A61M 2025/028; A61M 25/0026; A61M 25/02; A61M 3/0283; A61M 1/08; A61M 16/22; A61M 2025/0019; A61M 2025/0063; A61M 2025/024; A61M 2202/0496; A61M 2205/07; A61M 2205/106; A61M 2205/3327; A61M 2205/3331; A61M 2205/3379; A61M 2205/36; A61M 2205/3653; A61M 2210/1053; A61M 2210/1085; A61M 2210/1475; A61M 25/0017; A61M 25/0023; A61M 25/0043; A61M 25/0147; A61M 25/1034; A61M 3/0204; A61M 3/0254; A61M 3/0266; A61M 3/027; A61M 3/0279; A61M 3/0287; A61M 31/00; A61M 5/003; A61M 5/158; A61M 60/178; A61M 60/216; A61M 60/865; A61M 25/0015; A61M 25/1027–1038

USPC .......................................................... 606/194
See application file for complete search history.

(56) References Cited

U.S. PATENT DOCUMENTS

| | | | | |
|---|---|---|---|---|
| 5,454,788 | A * | 10/1995 | Walker | A61M 25/10 604/99.04 |
| 5,571,087 | A | 11/1996 | Ressemann et al. | |
| 5,951,929 | A * | 9/1999 | Wilson | A61M 25/0009 264/296 |
| 6,336,906 | B1 | 1/2002 | Hammarstrom et al. | |
| 6,503,353 | B1 * | 1/2003 | Peterson | A61M 25/005 604/524 |
| 7,931,603 | B2 * | 4/2011 | Von Malmborg | A61M 25/09 600/585 |
| 8,685,053 | B2 * | 4/2014 | Brown | A61M 25/10 623/1.11 |
| 9,138,565 | B2 | 9/2015 | Schwager et al. | |
| 2003/0069521 | A1 | 4/2003 | Reynolds et al. | |
| 2004/0106878 | A1 | 6/2004 | Skujins et al. | |
| 2007/0100374 | A1 | 5/2007 | Vrba | |
| 2012/0238872 | A1 | 9/2012 | Schwager | |

OTHER PUBLICATIONS

PCT/SE2018/050820, "International Preliminary Report on Patentability", dated Nov. 19, 2019, 14 pages.
PCT/SE2018/050820, "International Search Report and Written Opinion", dated Nov. 22, 2018, 15 pages.

* cited by examiner

PRESSURE CATHETER AND GUIDE WIRE ASSEMBLY

RELATED APPLICATIONS

This application is a U.S. National Stage of International Application No. PCT/SE2018/050820, filed Aug. 14, 2018, claiming priority to Swedish Patent Application No. 1750993-6, filed Aug. 15, 2017, the contents of which are hereby incorporated by reference in their entirety.

FIELD OF THE INVENTION

The present invention relates generally to a catheter and guide wire assembly for intravascular measurements of blood pressure in a living body, and more particularly to a catheter and guide wire assembly comprising a proximal tube, a distal tube, a fluid-permeable coil, a distal tip and a core wire, and relates even more particularly to a catheter and guide wire assembly wherein the proximal tube and the distal tube are connected by a butt joint, over which a shrinking tubing can be shrunk.

BACKGROUND OF THE INVENTION

Catheter and guide wire assemblies for intravascular blood pressure measurements in a living body are known in the art. These catheter and guide wire assemblies comprise typically a proximal and relatively rigid tubular member, which is connected to a distal and relatively more flexible tubular member, which, in turn, is connected to a fluid-permeable coil, which ends in a distal tip. To provide the catheter and guide wire assemblies with the necessary mechanical properties, a core wire is further arranged within the proximal tubular member and extends through the distal tubular member and the fluid-permeable coil, and is secured in the distal tip.

In use, a catheter and guide wire assembly of this type is filled with a fluid, typically saline, to create a fluid line from a distal portion, which, via the fluid-permeable coil, is in fluid connection with blood, to the proximal end, which is connected to an external pressure transducer. The external pressure transducer comprises a membrane, on which the blood pressure, via the fluid line, exerts a dynamic pressure, thereby causing a deflection of the membrane. The amount of deflection is converted to an electrical signal, the amplitude of which is converted to a pressure reading, which typically is displayed on a monitor or a similar device. From the above, it can be inferred that the diameter of the core wire is less than the inner diameters of the proximal tubular member, the distal tubular member and the fluid-permeable coil, respectively, to thereby provide the catheter and guide wire assembly with an inner lumen having cross-sectional dimensions large enough to provide a pressure-transmitting fluid line that enables good signal characteristics and allow efficient flushing of blood out of the catheter lumen.

Further, to maneuver a catheter and guide wire assembly in, for example, tortuous coronary arteries requires that the catheter and guide wire assembly has excellent guiding properties, i.e. a high torsional rigidity and a well-controlled bending stiffness that preferably varies along the length of the catheter and guide wire assembly. These mechanical properties are mainly determined and provided by the mechanical characteristics of the core wire. However, as the outer dimension of the catheter and guide wire assembly is limited by the use in small blood vessels and/or by standardized requirements set by, e.g., stent catheters, the overall requirements on a catheter and guide wire assembly—which should both function as a pressure transducer and a guide wire—are both demanding and inherently incompatible. That is, to design a catheter and guide wire assembly having good mechanical properties (i.e. a high torsional rigidity and a well-controlled and varying bending stiffness), which are mainly provided by a core wire, whose outer dimensions must be small enough to provide an inner lumen that is large enough to provide a pressure-transmitting fluid line having good signal characteristics, is a very challenging problem, which has not been fully addressed and met by the prior art; and despite the fact that a catheter and guide wire assembly should be a very useful and economically appealing tool for measuring blood pressure in a living body, such devices have never been generally accepted by the medical community.

An exemplifying catheter and guide wire assembly of this type is disclosed in the U.S. Pat. No. 9,138,565 to Schwager et al, wherein a catheter and guide wire assembly comprises a two-part hollow shaft connected to a flexible wire coil having a wire tip at the distal end thereof, and wherein a core wire is arranged in the lumen of the two-part hollow shaft to control the flexibility of the catheter and guide wire assembly. The two-part shaft comprises a distal portion and a proximal portion, which preferably has less elasticity than the distal portion of the two-part shaft. Here, it can be noted that the joint between the proximal portion and the distal portion is only schematically disclosed in an arrangement which can be improved regarding its mechanical properties.

Another exemplifying catheter and guide wire assembly is disclosed in the U.S. Pat. No. 4,964,409 to Tremulis, wherein a guiding member comprises a main tubular member, a tubular extension secured to the distal end of the main tubular member, a flexible body secured to the distal end of the tubular extension, and a core member, which is secured to the inner lumen of the main tubular member and extends through the tubular extension and into the flexible body. In this arrangement, the tubular extension is shorter than the main tubular member and is dimensioned to fit tightly over a distal portion of the main tubular member, something which thereby reduces the available inner lumen.

Considering the challenging and inherently incompatible requirements that a catheter and guide wire assembly has to fulfill, it is believed that the designs disclosed in the prior art still have shortcomings regarding the signal quality and reliability when the catheter and guide wire assembly operates as a pressure transducer and/or regarding the mechanical handling characteristics when the catheter and guide wire assembly is handled as a guide wire. An object of the present invention is therefore to provide a catheter and guide wire assembly whose mechanical handling characteristics match or exceed the mechanical characteristics of the catheter and guide wire assemblies known today and which, in use, provides blood pressure measurements, the reliability and accuracy of which match or exceed the reliability and accuracy of the catheter and guide wire assemblies known today.

SUMMARY OF THE INVENTION

The above-mentioned object is achieved by the present invention according to the independent claim. Preferred embodiments are set forth in the dependent claims.

The present invention is based on the insight about the importance of the design of the connections or joints between the different parts of a catheter and guide wire assembly, and the invention relates in particular to the connection between a proximal tubular member, which typically is relatively rigid, and a more distal tubular member, which typically is relatively flexible. Therefore, in accordance with a first embodiment of the invention, a catheter and guide wire assembly for measurement of blood pressure in a living body comprises a proximal tube having a distal end and a proximal end; a distal tube having a distal end and a proximal end, which is connected to the distal end of the proximal tube; a fluid-permeable coil having a distal end and a proximal end, which is connected to the distal end of the distal tube; a distal tip, in which the distal end of the fluid-permeable coil is secured; and a core wire, which is attached in the proximal tube and which extends through a portion of the proximal tube, the distal tube and the fluid-permeable coil, and is secured in the distal tip, wherein the distal end of the proximal tube and the proximal end of the distal tube are connected by a butt joint. Such a butt joint provides for an inner lumen having a maximal cross-sectional area, and, since the core wire is attached inside the proximal tube, provides also for the necessary torsional rigidity and bending stiffness for the catheter and guide wire assembly.

In one embodiment of the invention, the butt joint is a square butt joint, which facilitates easy manufacturing of the proximal and distal tubes; and in another embodiment of the invention, the butt joint is a beveled butt joint, which provides a larger contact surface between the proximal and distal tubes, upon which glue can be applied. The degree of bevelment is preferably relatively small and is characterized by an angle $\beta$ measured from a normal to the longitudinal axis of the catheter and guide wire assembly, where $0° \leq \beta \leq 30°$ (and $\beta=0°$ corresponds to a square butt joint).

For all embodiments presented and described herein, the butt joint is preferably enclosed by a shrinking tubing, which is shrunk over the butt joint, to provide a fluid-tight joint; and more specifically, the shrinking tubing is shrunk over a circumferential outer surface portion of the proximal tube and also over a circumferential outer surface portion of the distal tube, such that the shrinking tubing covers and encloses the butt joint. Preferably, the shrinking tubing extends at least 0.5 mm on each side of the butt joint (i.e. the shrinking tubing itself is at least 1 mm long).

As stated above, the core wire is attached in the proximal tube, i.e. the core wire is attached to an inner wall of the proximal tube; and in one embodiment of the invention, the core wire is glued to an inner wall of the proximal tube, which is an easy and reliable way of attaching the core wire to the proximal tube. To provide a reliable joint, the core wire is in a preferred embodiment attached, e.g. by gluing, in the proximal tube at or close to the butt joint. Similarly, in another embodiment of the invention, the core wire is attached, e.g. by gluing, in the distal tube at or close to the butt joint. In one embodiment, glue is provided such that the glue bridges over the butt joint and extends over portions of both the proximal and distal tubes, which provides for a strong and reliable butt joint. A point of attachment of the core wire at or close to the butt joint implies that the core wire does not extend an unnecessary long distance into the proximal tube and/or into the distal tube, which, in turn, means that the core wire occupies a minimal portion of the inner lumen of the proximal tube and/or of the inner lumen of the distal tube, to thereby provide for a fluid line with good signal characteristics.

In one embodiment, the core wire extends between about 5 mm to about 500 mm, more preferably 5 mm to 100 mm and even more preferably 10 mm to 50 mm into the proximal tube from the butt joint.

In one embodiment of the invention, the proximal tube has a wall thickness of more than about 0.040 mm, to avoid that the proximal tube easily kinks.

In another embodiment of the invention, the distal tube has a wall thickness of less than about 0.050 mm, to provide for good torque response in the catheter and guide wire assembly.

BRIEF DESCRIPTION OF THE DRAWINGS

The present invention will be further explained hereinafter by means of non-limiting examples and with reference to the appended drawings, wherein:

FIG. 1b is an enlarged view of the butt joint in FIG. 1a;

FIG. 2b is an enlarged view of the butt joint in FIG. 2a.

DETAILED DESCRIPTION OF PREFERRED EMBODIMENTS

Figure 1A:
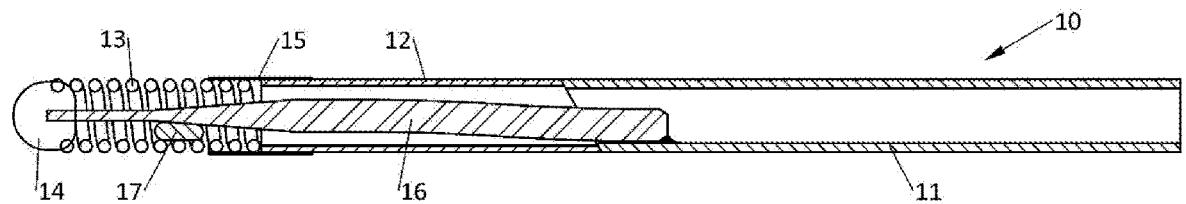
FIG. 1a is a schematic cross-sectional illustration of a first embodiment of a catheter and guide wire assembly according to the invention, wherein a proximal tube and a distal tube have been joined together by a butt joint.

FIG. 1a illustrates schematically a cross-sectional view of a catheter and guide wire assembly 10 according to an embodiment of the invention. The catheter and guide wire assembly 10 comprises a proximal tube 11 having a distal end and a proximal end. The proximal end of the proximal tube 11 is connectable to an external pressure transducer. Such an external pressure transducer is well-known in the art and will not be further described herein. The catheter and guide wire assembly 10 comprises further a distal tube 12 having a distal end and a proximal end, which is connected to the distal end of the proximal tube 11 in a way that will be thoroughly described below. The distal end of the distal tube 12 is connected to a proximal end of a fluid-permeable coil 13, which has a distal end that is connected to and secured in a distal tip 14, which can be rounded or dome-shaped. In the embodiment shown in FIG. 1a, the connection between the distal tube 12 and the fluid-permeable coil 13 is covered and enclosed by a shrinking tubing 15, which has been shrunk and preferably also glued over the connection or contact area, to provide a more reliable joint between the distal tube 12 and the fluid-permeable coil 13. A shrinking tubing, such as shrinking tubing 15, arranged over a connection or joint between a distal tube and a fluid-permeable coil can optionally be arranged for all embodiments presented herein.

From FIG. 1a, it can be appreciated that the proximal tube 11, the distal tube 12 as well as the fluid-permeable coil 13 all are hollow, so as to provide an interior fluid line extending from the fluid-permeable coil 13 to the proximal end of the proximal tube 11. To provide the necessary mechanical strength, bending stiffness and torsional rigidity for the catheter and guide wire assembly 10, a core wire 16 is arranged inside the inner lumen of the catheter and guide wire assembly 10; and more specifically, the core wire 16 is attached, e.g. by gluing or brazing, at an inner wall of the proximal tube 11 and extends through the distal tube 12 and the fluid-permeable coil 13, and is secured in the distal tip 14. It can further be appreciated that the core wire 16 is attached in a portion of the fluid-permeable coil 13. Such an attachment 17, can optionally be arranged for all embodiments presented herein and can be accomplished with, for example, brazing or gluing, and contributes favorably to the mechanical properties of a catheter and guide wire assembly according to the invention.

Figure 1B:
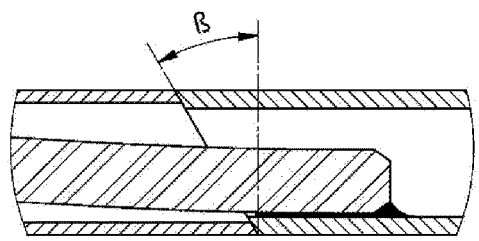

As was stated above, the present invention is based on the insight about the importance of the specific design of the connections between different parts of a catheter and guide wire assembly, because such connections should transfer mechanical properties between different parts of a catheter and guide wire assembly without unnecessarily reduce the available area of an inner lumen, which is necessary to provide a fluid line having good signal characteristics, wherein the specific design of a connection between two parts is even more crucial for small outer diameters of the catheter and guide wire assembly in question, e.g. for a standardized outer diameter of about 0.014 inches (about 0.36 mm). FIG. 1b illustrates the connection between the proximal tube 11 and the distal tube 12 of the catheter and guide wire assembly 10 described above in conjunction with FIG. 1a. As can be seen in FIG. 1b, the connection between the proximal tube 11 and the distal tube 12 is implemented in the form of a butt joint. Such a butt joint does not reduce the inner cross-sectional area of the inner lumen at the position of the butt joint. It can further be appreciated that since the core wire 16 is attached inside the proximal tube 11 and is also secured in the distal dome-shaped tip 14 and, optionally, also in the fluid-permeable coil 13, a reliable and strong joint between the proximal tube 11 and the distal tube 12 has thereby been accomplished.

The butt joint between the proximal tube 11 and the distal tube 12 can be a square butt joint or a beveled or angled butt joint, and in FIG. 1b this feature is illustrated by the bevelment angle $\beta$, which in accordance with the invention is such that $0° \leq \beta \leq 30°$, and $\beta = 0°$ corresponds to a square butt joint. It can further be noted that the core wire 16 is attached to an inner wall of the proximal tube 11, such that there is a gap or small distance between the point of attachment, which preferably is accomplished by gluing, and the butt joint between the proximal tube 11 and the distal tube 12. This gap is merely introduced to demonstrate that, for example, glue does not have to be applied all the way to the butt joint.

Figure 2A:
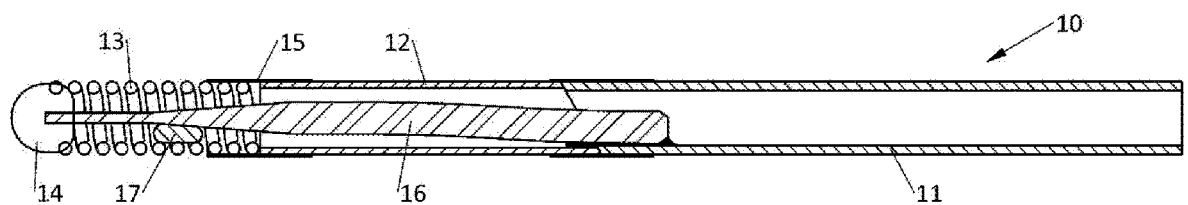
FIG. 2a is a schematic cross-sectional illustration of a second embodiment of a catheter and guide wire assembly according to the invention, wherein a proximal tube and a distal tube have been joined together by a butt joint, over which a shrinking tubing has been shrunk.

FIG. 2a illustrates schematically another embodiment of a catheter and guide wire assembly, wherein similar or identical components have been given the same reference numerals as in FIG. 1a and FIG. 1b, respectively. As in the embodiment disclosed in FIGS. 1a and 1b, a catheter and guide wire assembly 10 for measurement of blood pressure in a living body comprises a proximal tube 11 having a distal end and a proximal end, a distal tube 12 having a distal end and a proximal end, which is connected to the distal end of the proximal tube 11, a fluid-permeable coil 13 having a distal end and a proximal end, which is connected to the distal end of the distal tube 12, a distal tip 14, in which the distal end of the fluid-permeable coil 13 is secured, and a core wire 16, which is attached in the proximal tube 11 and which extends through a portion of the proximal tube 11, the distal tube 12 and the fluid-permeable coil 13, and is secured in the distal tip 14, wherein the distal end of the proximal tube 11 and the proximal end of the distal tube 12 are connected by a butt joint. As is best seen in FIG. 2b, also in this embodiment, the butt joint can be a square butt joint or a beveled or angled butt joint, as is indicated by the angle $\beta$, which is such that $0° \leq \beta \leq 30°$, and $\beta = 0°$ corresponds to a square butt joint.

Figure 2B:
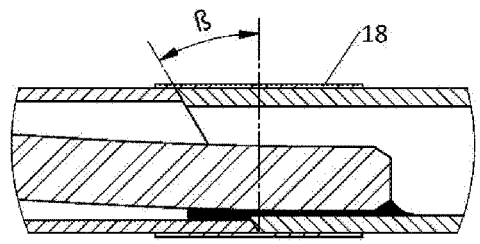

The butt joint between the proximal tube 11 and the distal tube 12 is illustrated in an enlarged view in FIG. 2b, wherein it can further be seen that the butt joint is covered and enclosed by a shrinking tubing 18, which is shrunk over the butt joint, i.e. the shrinking tubing has been threaded over the catheter and guide wire assembly 10 and advanced to the position of the butt joint and has thereafter been exposed to heat, to heat-shrink to shrinking tubing 18 over the butt joint, to thereby provide a fluid-tight joint, which ensures that fluid only enters the catheter and guide wire assembly 10 via the fluid-permeable coil 13. Preferably, the shrinking tubing 18 extends at least 0.5 mm on both the proximal side and the distal side of the butt joint, i.e. the shrinking tubing is preferably at least 1 mm long. Preferably, the shrinking tubing 18 is also glued to the proximal tube 11 and the distal tube 12. Here, it should be emphasized that a shrinking tubing 18 also can be provided for the embodiment described above in conjunction with FIG. 1a and FIG. 1b.

From FIG. 2a and especially from FIG. 2b, it can also be seen that in this embodiment the core wire 16 is attached also in the distal tube 12. That is, the core wire 16 is, for example, glued to an inner wall of the distal tube 12, where the point of attachment can be at virtually any distance from the butt joint, but it is preferred that the core wire 16 is attached, e.g. glued, to an inner wall of the distal tube 12 at or close to the butt joint. As was indicated already above, in conjunction with FIGS. 1a and 1b, the core wire 16 is also attached, e.g. glued, to an inner wall of the proximal tube 11 at or close to the butt joint; and in FIG. 2b it can be seen that in this particular embodiment, the glue forms a bridge over the butt joint. Preferably, the core wire 16 extends between about 5 mm to about 500 mm, more preferably 5 mm to 100 mm and even more preferably 10 mm to 50 mm into the proximal tube 11 from the butt joint. By limiting the extension of the core wire 16 into the proximal tube, the core wire 16 occupies the inner lumen of the proximal tube 11 in a minimal length portion of the proximal tube 11, which provides for a fluid line with good signal characteristics. By attaching the core wire 16 to the inner wall of the proximal tube 11 at or close to the butt joint, the torque response of the catheter and guide wire assembly is improved, since the proximal tube 11 transfers the torque instead of the core wire 16 proximal to the attachment of the core wire 16 to the proximal tube 11. Preferably, the core wire 16 is attached to the inner lumen of the proximal tube 11 from the butt joint and between 5 mm and 500 mm, more preferably 5 mm to 100 mm and even more preferably 10 mm to 50 mm into the proximal tube 11.

For all embodiments, or combinations of embodiments, presented herein, the following exemplifying dimensions and materials can be used: The proximal tube 11 comprises a hollow and relatively stiff tube made from, e.g., stainless steel, and has a length in the interval of about 1200 mm to 2000 mm, and an inner diameter in the interval of about 0.2 mm to 0.3 mm, and more preferably 0.2 mm to 0.26 mm and an outer diameter of about 0.35 mm. Although a large inner lumen is advantageous for creating a fluid line with good signal characteristics, the inner lumen of the proximal tube 11 cannot be too large since a too large inner lumen will make the proximal tube 11 prone to kinking instead of bending during extensive handling in clinical use. A kinked proximal tube will easily break apart and is therefore unsuited for clinical use. Tests have shown that the tendency to kink is surprisingly sensitive to the inner diameter of the proximal tube 11, or rather to the wall thickness of the proximal tube 11; and in one embodiment of the invention the inner lumen of the proximal tube 11 does not exceed 0.26 mm, to thereby provide the proximal tube 11 with a wall thickness of more than about 0.040 mm.

The distal tube 12 comprises a hollow and relatively flexible tube (i.e. a tube having a relatively low bending stiffness) made from, e.g., polyimide, polyamide or polyurethane, or any compounds thereof, and has a length in the interval of about 120 mm to about 500 mm, and an inner diameter in the interval of 0.26 mm to about 0.31 mm and an outer diameter of about 0.34 mm. It is preferred to keep the inner diameter of the distal tube 12 at or above 0.25 mm to secure that the complete catheter and guide wire assembly is flexible enough in its distal part and can align with arteries and avoid straightening them. A thin-walled distal tube 12 will also provide better torque response compared to a thick-walled distal tube 12 since a larger amount of plastic material will reduce torque response transmitted by the core wire 16 from the proximal to the distal end of the total catheter and guide wire assembly. Thus, in one embodiment of the invention, the wall thickness of the proximal tube 15 is less than about 0.050 mm.

The coil 13 comprises a flexible and hollow coil made from, e.g., platinum, palladium or tungsten, or any alloys thereof, and has a length in the interval of about 15 mm to about 45 mm, and an inner diameter in the interval of about 0.16 mm to about 0.26 mm. The core wire 16 is a solid metal wire made from, e.g., stainless steel, and has length in the interval of about 140 mm to about 745 mm. The core wire 16 can have a diameter that varies along its length, i.e. the core wire 16 can be a tapered wire, but generally the diameter of the core wire 16 is in the interval from about 0.20 mm to about 0.04 mm. The core wire 16 can be attached to the proximal tube 11 by gluing, e.g. with the use of epoxy, cyanoacrylates or polyurethanes; and if the core wire 16 is also attached to the distal tube 12 and/or to the coil 13, such an attachment 17, can also be made with brazing or gluing, e.g., with the use of epoxy, cyanoacrylates or polyurethanes. The outer diameter of the catheter and guide wire assembly 10 can vary from a few tenths of a millimeter to a few millimeters, but is typically about 0.014 inches (about 0.36 mm), which is standard dimension within the field, wherein the thickness of the shrinking tubing 18 is considered having a negligible contribution to the outer diameter of the catheter and guide wire assembly, when the shrinking tubing 18 is incorporated in the catheter and guide wire assembly 10. The shrinking tubing 18 is made from e.g. polyester or polytetrafluoroethylene (PTFE). The same considerations apply for the more distal shrinking tubing 15. Thus, the present invention is particularly useful for a catheter and guide wire assembly having an outer diameter of about 0.014 inches (about 0.36 mm).

Although the present invention has been described with reference to specific embodiments, also shown in the appended drawings, it will be apparent to those skilled in the art that many variations and modifications can be done within the scope of the invention as described in the specification and defined with reference to the claims below.

The invention claimed is:

1. A catheter and guide wire assembly (10) for measurement of blood pressure in a living body, comprising:
   a proximal tube (11) having a distal end and a proximal end;
   a distal tube (12) having a distal end and a proximal end, which is connected to the distal end of the proximal tube (11);
   a fluid-permeable coil (13) having a distal end and a proximal end, which is connected to the distal end of the distal tube (12);
   a distal tip (14), in which the distal end of the fluid-permeable coil (13) is secured; and
   a core wire (16), which is attached in the proximal tube (11) and which extends through a portion of the proximal tube (11), the distal tube (12) and the fluid-permeable coil (13), and is secured in the distal tip (14), wherein the proximal tube (11), the distal tube (12), and the fluid-permeable coil (13) are all hollow, and provide an interior fluid line extending from the fluid-permeable coil (13) to the proximal end of the proximal tube (11), characterized in that an outer diameter of the catheter and guide wire assembly (10) is about 0.014 inches (about 0.36 mm) and that the distal end of the proximal tube (11) and the proximal end of the distal tube (12) are connected by a butt joint and wherein the core wire (16) is glued to the inner wall of the proximal tube (11) at the butt joint and the core wire (16) is glued to an inner wall of the distal tube (12) at the butt joint, such that the glue bridges over the butt joint, and wherein a shrinking tubing (18) is shrunk over the butt joint and glued to the proximal tube (11) and the distal tube (12).

2. The catheter and guide wire assembly (10) according to claim 1, wherein the butt joint is a square butt joint, or a beveled butt joint with a bevelment angle β such that $0° \leq \beta \leq 30°$.

3. The catheter and guide wire assembly (10) according to claim 1, wherein that the shrinking tubing (18) extends at least 0.5 mm on the proximal and distal sides of the butt joint.

4. The catheter and guide wire assembly (10) according to claim 1, wherein the wall thickness of the proximal tube (11) is larger than about 0.040 mm.

5. The catheter and guide wire assembly (10) according to claim 1, wherein the wall thickness of the distal tube (12) is less than about 0.050 mm.

* * * * *